United States Patent [19]
Ashani et al.

[11] Patent Number: 4,472,320
[45] Date of Patent: Sep. 18, 1984

[54] DIOXAPHOSPHORINANES

[76] Inventors: Yacov Ashani, 10 Kazanelson St., Rishon Lezion 75218; Haim Leader, 5 Simtat Hamaaloth St., Ramat Hasharon 47273; Lily Raveh, 15 Trachtenberg St., Rishon Lezion 75283; Rachel Bruckstein, 34 Emek Bracha St., Tel Aviv; Michael Spiegelstein, 3 S Ben Zion St., Rehovot 76451, all of Israel

[21] Appl. No.: 378,815

[22] Filed: May 17, 1982

[30] Foreign Application Priority Data

Jun. 4, 1981 [IL] Israel ......................................... 63037

[51] Int. Cl.³ ................................................. C07F 9/21
[52] U.S. Cl. ..................................... 260/937; 424/209
[58] Field of Search ................................ 260/936, 937

[56] References Cited

U.S. PATENT DOCUMENTS 4,035,448  7/1971  Mayerhoefer et al. ............. 260/937

OTHER PUBLICATIONS

Leader et al., "Chem. Abs.", vol. 96, (1982) 156812j, from ACS Symp. Ser. 1981, 171 (Phosphorous Chem.), 179–182.

Primary Examiner—Anton H. Sutto
Attorney, Agent, or Firm—Browdy and Neimark

[57] ABSTRACT

There are provided dioxaphosphorinane compounds, a process for the production of these and compositions containing same. These are non-toxic anticholinesterase drugs for the treatment of organophosphorus poisoning, and for the treatment of cholinergic diseases.

5 Claims, No Drawings

DIOXAPHOSPHORINANES

FIELD OF THE INVENTION

The present invention relates to novel dioxaphosphorinane compounds, to their synthesis and to compositions containing same, as non-toxic anticholinesterase drugs to be used in medicine.

BACKGROUND OF THE INVENTION

In recent studies it has been shown that eel acetylcholinesterase (AChE, EC 3.1.1.7) previously inhibited with 1,3,2-dioxaphorinane 2-oxides undergoes spontaneous reactivation with a $t_{\frac{1}{2}}=12$ minutes at pH 7.0 in marked contrast to enzyme inhibited with O,O-diethylphosphoryl derivatives, see Ashani et al Biochemistry 11, 3518 (1972) and Ashani and Leader, Biochem.J. 177, 781 (1979).

The protection of mammals against poisoning by organo-phosphorus compounds by pretreatment with carbamates have been attributed to inhibition of acetylcholinesterase (AChE, EC 3.1.1.7) by forming labile carbamoyl-AChE conjugates. This inhibition prevents complete and irreversible phosphorylation and consequently enzyme activity is restored due to spontaneous decarbamoylation. The rate of AChE regeneration depends amongst others on the structure of the carbamoyl moiety and on the kinetic properties of the enzyme, see f. f. Gordon et al Toxicol and App. Pharmacol. 43, 207 (1978).

In addition, carbamates are commonly used for the treatment of diseases that are associated with cholinergic disorders, e.g. pyridostigmine bromide in Myasthenia Gravis, neostigmine methylsulphate in neurogenic bladder dysfunctions and physostigmine in brain disorders.

Carbamates of this type are rather toxic drugs and the maximum dosage which does not result in side-effects for compounds such as physostigmine sulfate and pyridostigmine iodide in guinea pigs is 0.1 mg/kg respectively.

SUMMARY OF THE INVENTION

The present invention relates to novel compounds of the formula

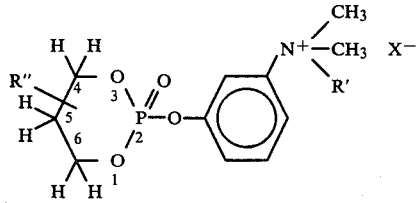

where R' is H alkyl, aryl, aralkyl or a group -alkyl-N(R')$_2$, R" is H or an alkyl group positioned either at the 4,5 or 6 position of the dioxaphosphorinane ring, where X is a physiologically acceptable anion to the corresponding quaternary or free amine, to a process for the production of such compounds, and to pharmaceutical compositions of matter which contain such compound or compounds as active ingredient to be used in the treatment of cholinergic disorders and prophylaxis against organophosphorus poisoning.

The pharmaceutical compositions are of value in the treatment of poisoning by organo-phosphorus compounds and also in the treatment of diseases such as Myasthenia gravis (and other similar autoimmune diseases), glaucoma, bladder dysfunction, brain disorders and general analeptics.

In contrast to carbamates the novel compounds are comparatively non-toxic and can be administered in comparatively large dosages without undue side-effects.

Compounds according to the above general formula are easily prepared, as is exemplified by the following example.

Compounds of choice are compounds wherein R' is lower alkyl such as methyl, ethyl, propyl, isopropyl, butyl, isobutyl, tert-butyl; aryl such as phenyl, substituted phenol, benzyl, etc., where R" is hydrogen, methyl, ethyl, propyl, isopropyl, X is any conventional physiologically acceptable anion. Preferred anions are halogens such as chlorine, bromine, iodine, and methansulphonate.

The novel compounds are actually a synthesis of two moieties (I) and (II), namely the cyclic phosphate ester (I) and the (3-trimethylammonio) phenyl iodide or similar group:

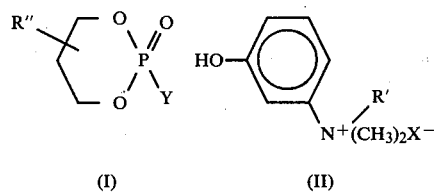

(I)          (II)

wherein Y designates in this type of esters Cl,F,SCH$_2$CH$_2$N(R')$_2$ etc. where R' is H,alkyl, aryl etc., R" is hydrogen or alkyl as defined above, and where X is as defined above.

The group (II) is a potential efficient leaving group. A preferred compound is O-(3-trimethylammoniophenyl) 1,3,2-dioxaphosphorinane 2-oxide iodide (TDPI), which is the combination product of the above compound (I) and of the compound (II) (R'=CH$_3$, X=I)

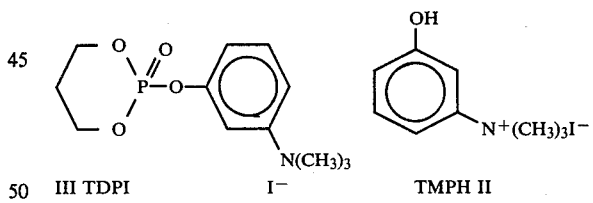

III TDPI         TMPH II

The preferred compound is the one wherein X is I$^-$; but any other physiologically acceptable anion can be used.

The introduction of the quaternary nitrogen increases the rate of inhibition while simultaneously the phosphorylation of AChE in vivo is restricted to peripheral sites. It has been found experimentally that the reversible phosphorylation of AChE by (I) may be controlled efficiently by specific reactivators, such as oximes, in contrast with the carbamoyl-AChE conjugate. The leaving group (II) is a structural analogue of the potent reversible inhibitor of AChE edrophonium bromide wherein R' is ethyl. Generally phenyl esters of the type (I) are very stable in neutral aqueous solutions at moderate temperatures (25°–37° C.).

The process of the present invention for the production of compounds of the formula III comprises reacting 2-substituted 1,3,2-dioxaphosphorinane 2-oxide (I, with X=Cl) with 3-dimethylaminophenol or with substituted 3-dimethylaminophenol followed by a further reaction with an alkyl halide such as methyl iodide to produce the desired product.

The novel compounds are of value as active ingredient of pharmaceutical compositions, for treatment of cholinergic disorders and prophylaxis against poisoning by organophorphorus compounds. For example, a prophylactic application of such compositions has resulted in a protective effect against dosage of the order of from 5 to 22 $LD_{50}$ expressed in terms of protective ratio depending on the poison administered and animal used. Furthermore, the novel compounds and pharmaceutical compositions containing same are of value in the treatment of diseases where controlled increase of acetylcholine is expected to be effective in the management of cholinergic disorders. For example compound of type III increased significantly the contractibility of smooth muscle taken from the bladder dome of rabbit and humans. It also protected the pretreated hemidiaphragm of rats from soman poisoning by partial and temporary block of AChE.

The invention is illustrated by means of the synthesis and use of a specific compound of the above group of compounds, namely the compound wherein R is methyl and where X is a halogen, preferably iodine. It is to be clearly understood that this is by way of example only and that the other compounds are of similar utility and can be prepared by an analogous route, which is clear to the chemists versed in this field of chemistry.

Anal.: Calc for $C_{12}H_{19}NPO_4I$ C,36.09; H,4.76; N,3.50
Found: C,35.96; H,4.73; B,3.32

NMR, MS and IR spectroscopy confirmed the homogeneity and structure of TDPI.

UV analysis indicates that the free phenol TMPH, if present at all, does not exceed 0.3%.

By using the above process the cis-and trans- 4-methyl derivatives of III, namely of O-(3-trimethylammoniophenyl) 4-methyl-1,3,2-dioxaphosphorinane 2-oxide iodide, were prepared. The two isomers were separated by column chromatography prior to the alkylation to methyl iodide.

The novel compound (III) wherein $R'=CH_3$, $R''=H$ in positions 4,5 and 6, and X=I,(TDPI) was incubated with AChE either from electric eel or rat-brain homogenate and the decrease in enzyme activity approached a steady state. The initial rate of release of TMPH was found to be in good agreement with the rate of constant obtained from inhibition measurements. The inhibited enzyme recovered spontaneously upon extensive dilution at a rate similar to the rate constants calculated from the inhibition studies of Scheme I.

2-hydroximinomethyl-1-methylpyridinium iodide (2-PAM) accelerated significantly the spontaneous reactivation whereas the 3 analog (3-PAM) did not enhance the regeneration of enzyme activity. On the basis of these results and comparative evaluation with previous studies, where different cyclic esters (I) were utilized the following scheme for the inhibition of AChE by TDPI is suggested:

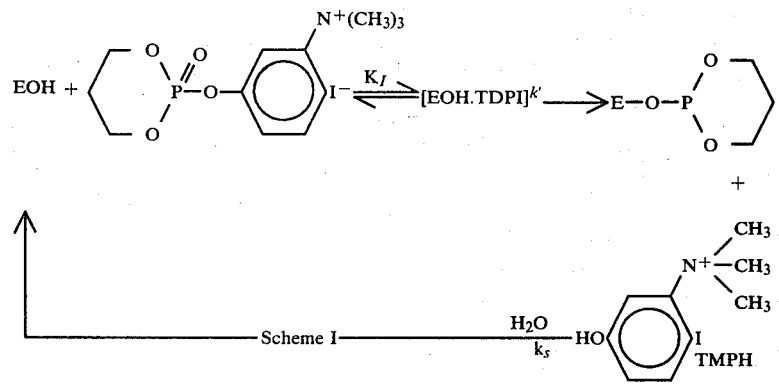

EXAMPLE

Preparation of O-3-trimethylammoniophenyl 1,3,2,-dioxaphosphorinane 2-oxide iodide (TDPI)

(a) A solution of 2-chloro-1,3,2-dioxaphosphorinane 2-oxide (48.0 g, 0.3M) in dry benzene was added dropwise to solution of 3-N,N-dimethylaminophenol (42.0 g, 0.3M) and triethylamine in 250 ml of dry benzene. The mixture was refluxed for 4 hours, cooled to room temperature and filtered off the triethylamine HCl. After washing with cold water followed by cold 10% aqueous NaOH, the benzene was dried over $MgSO_4$ and removed under reduced pressure. The resulting viscous oil was chromatographed on silica ($CHCl_3$) to give 31.5 g of the pure and homogenous tertiary amine.

(b) 11.0 g of foregoing preparation and 20 g methyliodide were refluxed in acetone for 2 hours. The precipitate was filtered off and recrystallized from 95% ethanol to give 8.9 g pale yellow rhombic crystals m.p. 178°–181° C. (dec).

Butyrylcholinesterase (BuChE, EC 3.1.1.8) from either horse or mice serum displayed different profiles. Steady state was not developed, although the rate constants of inhibition decreased with time. Since the presence of multiforms of serum BuCHE has been established it is likely that the first order plot represents more than one exponent. The inhibited enzyme did not regenerate as fast as AChE-TDPI conjugate. However, 2-PAM enhanced the reactivation of horse serum BuChE after inhibition with TDPI. The various rate constants were computed from the initial slopes of the inhibition and reactivation of BuChE in contrast to AChE where the individual constants were computed from equations derived on the basis of Scheme I. Aging was observed only in the case of BuChE. Table 1 summarizes several kinetic parameters associated with the inhibition of AChE and BuChE by TDPI.

TABLE

| Enzyme | Kinetic Parameters for TDPI at pH 7.0 | | | |
|---|---|---|---|---|
| | $k_i(M^{-1} min^{-1})^a$ | $k_S(min^{-1})^b$ | $k_r(min^{-1})^c$ | %-aging[d] |
| AChE, eel | $8.4 \times 10^3$ | 0.07 | 0.38 | 2 |
| BuChE, horse | $1.8 \times 10^4$ | 0.005 | 0.05 | 69 |

[a] $k_i = k'/K_I$ (Scheme 1);
[b] From direct measurements;
[c] 0.5 mM 2-PAM. $k_S$ substracted;
[d] After 20 hr in presence of 0.5 mM TDPI.

The formation of unstable covalent phosporyl-AChE conjugate is evidently accompanied by non-covalent reversible complex (Michaelis complex) between AChE and TDPI (AChE.TDPI) or TMPH (AChE.TMPH). Although TMPH ($K_I=0.25$ μM) was found to be 50-fold more powerful than TDPI ($K_I=0.013$ mM) in terms of concentration required to achieve similar amount of Michalis complex, TDPI provided better protection of AChE against irreversible phosphroylation than II. In this set of experiments the efficiency of TDPI and TMPH were compared on the basis of equal concentration/affinity ratio were $I/K_I=10$.

When TDPI was added to an isolated rat-hemidiaphragm, AChE activity decreased at a rate similar to AChE from either rats-brain homogenate or electric eel. Removal of TDPI by washing restored the activity of the enzyme in rat-hemidiaphragm to the original level within 15–30 minutes. TDPI protected the rat-hemidiaphragm from irreversible block of tetanic tension, caused by the powerful anticholinesterase inhibitor 1,2,2-trimethylpropyl methylphosphonofluoridate (Soman). In hemidiaphragms that were not pre-treated with TDPI tetanic activity was abolished completely and could not be restored upon removal of the inhibitors. In addition, TDPI protected mice (in conjunction with anticholinergics and oxime) against $5 \times LD_{50}$ soman and $22 \times LD_{50}$ paraoxon.

The correlation between in vitro findings and in vivo observations suggest that the excellent protection of AChE provided by TDPI is due to the formation of reversible covalent-phosphoryl conjugate and reversible non-covalent Michaelis complexes, (AChE.TDPI) and (AChE.TMPH).

It was also demonstrated that smooth muscle taken from the detrusor (bladder dome) of either rabbit or human were highly responsive to TDPI. Thus muscles incubated for 10 min in the presence of 20 micrograms/ml TDPI contracted 5×stronger than non-treated muscle, upon the addition of same amount of acetylcholine. The muscle activity returned gradually to its normal activity upon washout. The toxicity of TDPI in terms of $LD_{50}$ was found to be 444 mg/kg (sc) in mice. TDPI is a relatively non-toxic potential drug, that may be applied for treatments of cholinergic impairments.

In another example it was shown that the introduction of one methyl group at the 4-position of compound (III) ($R'=CH_3$; 4-$R''=CH_3$ X=I), cis to the aryloxy moiety (II) increased the affinity of (III) to AChE ($K_I$) and produced a decrease in $k_S$ (See Scheme 1). In the case of the isomer having a 4-trans-methyl group the affinity, phosphorylation and spontaneous reactivation decreased significantly relative to TDPI. The acute toxicity ($LD_{50}$) of both 4-methyl isomers were found to be in the range of 210–260 mg/kg (sc in mice).

Since $K_I$, $k'$ and $k_S$ determine the overall rate constant for the approach to steady state of AChE and the activity of AChE at steady state compounds of type III can be considered as non-toxic drugs for treatment of diseases where controlled increase of acetylcholine is effective.

We claim:

1. A 1,3,2-dioxaphosphorinane 2-oxide derivative of the general formula

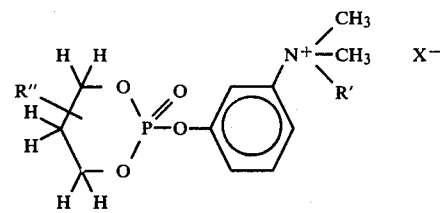

where R' designates hydrogen or alkyl
where R" is hydrogen or alkyl at positions 4,5 or 6, and
where X designates a physiologically acceptable anion.

2. The compound 3-trimethylammoniophenyl-1,3,2-dioxaphosphorinane 2-oxide, where X is a defined in claim 1.

3. A compound according to claim 2, wherein X is iodide.

4. A compound according to claim 1, wherein R" is methyl, ethyl, propyl, isopropyl, butyl, isobutyl and wherein R' is hydrogen.

5. A compound according to claim 1, wherein R' is alkyl and R" is lower alkyl or H.

* * * * *